United States Patent
Lundy, Jr. et al.

[11] Patent Number: 6,098,616
[45] Date of Patent: *Aug. 8, 2000

[54] NON-LINEAR NASAL DILATOR

[75] Inventors: Charles E. Lundy, Jr., Germantown, Tenn.; Jerome D. Muchin, Los Angeles, Calif.; Gary C. Wildman, Germantown, Tenn.

[73] Assignees: Acutek International, Inglewood, Calif.; Schering-Plough Healthcare Products Inc., Memphis, Tenn.

[ * ] Notice: This patent issued on a continued prosecution application filed under 37 CFR 1.53(d), and is subject to the twenty year patent term provisions of 35 U.S.C. 154(a)(2).
This patent is subject to a terminal disclaimer.

[21] Appl. No.: 09/042,437

[22] Filed: Mar. 13, 1998

[51] Int. Cl.⁷ .................................................. A61M 15/00
[52] U.S. Cl. ................................ 128/200.24; 128/206.25; 606/199
[58] Field of Search .......................... 128/200.24, 207.14, 128/DIG. 26, 858, 206.11, 206.24, 206.25; 606/199, 204.45

[56] References Cited

U.S. PATENT DOCUMENTS

| | | |
|---|---|---|
| Re. 35,408 | 12/1996 | Petruson . |
| 142,477 | 9/1873 | James . |
| D. 310,565 | 9/1990 | Petruson . |
| 701,538 | 6/1902 | Carence . |
| 850,978 | 4/1907 | Soares . |
| 1,043,924 | 11/1912 | Gottlieb . |
| 1,134,993 | 4/1915 | Bye . |
| 1,256,188 | 2/1918 | Wilson . |
| 1,292,083 | 1/1919 | Sawyer . |

(List continued on next page.)

FOREIGN PATENT DOCUMENTS

| | | |
|---|---|---|
| 242553 | 5/1961 | Australia . |
| 0 333 749 B1 | 9/1989 | European Pat. Off. . |
| 0 375 810 A1 | 7/1990 | European Pat. Off. . |
| 394505 | 3/1909 | France . |
| 630889 | 12/1927 | France . |

(List continued on next page.)

OTHER PUBLICATIONS

Petruson, Bjorn; "Improvement of the Nasal Airflow by the Nasal Dilator Nozovent", *Rhinology*, vol. 26, pp. 289–222 (1988).

Petruson, Bjorn; Letter to the Editor; "Better Sleep with Dilated Nose", *Rhinology*, vol. 27, pp. 211–213 (1989).

Petruson, Bjorn; "Decreased Nasal Resistance by the Nasal Dilator Nozovent® can Reduce Snoring", World Congress on Chronic Rhonchopathy, pp. 1–4 (May 1989).

Hoijer, Ulf et al.; "The Effects of Nasal Dilation on Snoring and Obstructive Sleep Apnea", *Archives of Otolaryngooogy—Head & Neck Surgery*, vol. 118, pp. 281–284 (Mar. 1992).

(List continued on next page.)

*Primary Examiner*—Aaron J. Lewis
*Attorney, Agent, or Firm*—Oppenheimer, Wolff & Donnelly, LLP

[57] ABSTRACT

A nasal dilator for preventing outer wall tissue of nasal passages of a nose from drawing in during breathing. There is an arcuate spring member for bridging a human nose, the spring member extending over the bridge and at least partly beyond the bridge on both sides of the bridge. An arcuate pad with an adhesive surface covers the spring member and extends around the spring member so that there is a perimeter of space formed between the spring member and the pad member. The spring is inset centrally in the pad. An adhesive between the spring member and the pad wholly connects the spring member on its entire engaging surface with the pad. The pad may include a protrusion to facilitate centralizing the dilator on the nose in use and there can be several overlapping release liners to facilitate use of the dilator.

11 Claims, 3 Drawing Sheets

U.S. PATENT DOCUMENTS

| | | |
|---|---|---|
| 1,322,375 | 11/1919 | Un . |
| 1,950,839 | 3/1934 | Chirila . |
| 1,950,926 | 3/1934 | Lobl . |
| 2,001,862 | 5/1935 | Battey . |
| 2,055,855 | 9/1936 | Weaver . |
| 2,221,758 | 11/1940 | Elmquist . |
| 2,243,360 | 5/1941 | Slatis et al. . |
| 2,264,153 | 11/1941 | Rowe . |
| 2,273,873 | 2/1942 | Klein . |
| 2,274,997 | 3/1942 | Thurman . |
| 2,277,390 | 3/1942 | Crespo . |
| 2,398,073 | 4/1946 | Bonde . |
| 2,426,161 | 8/1947 | Biederman . |
| 2,509,157 | 5/1950 | Lind . |
| 2,566,148 | 8/1951 | Sky . |
| 2,586,219 | 2/1952 | Geffas . |
| 2,625,931 | 1/1953 | Phillips . |
| 2,674,245 | 4/1954 | Tanditter . |
| 2,715,904 | 8/1955 | Hill . |
| 2,949,443 | 8/1960 | Merriam et al. . |
| 3,027,897 | 4/1962 | Carofiglio . |
| 3,046,989 | 7/1962 | Hill . |
| 3,426,751 | 2/1969 | Radewan . |
| 3,531,090 | 9/1970 | Laible . |
| 3,742,943 | 7/1973 | Malmin . |
| 3,747,597 | 7/1973 | Olivera . |
| 3,802,426 | 4/1974 | Sakamoto . |
| 3,835,848 | 9/1974 | Berner . |
| 3,905,335 | 9/1975 | Kapp . |
| 3,935,859 | 2/1976 | Doyle . |
| 4,153,051 | 5/1979 | Shippert . |
| 4,181,127 | 1/1980 | Linsky et al. . |
| 4,201,217 | 5/1980 | Slater . |
| 4,213,452 | 7/1980 | Shippert . |
| 4,220,150 | 9/1980 | King . |
| 4,221,217 | 9/1980 | Amezcua . |
| 4,267,831 | 5/1981 | Aguilar . |
| 4,274,402 | 6/1981 | Shippert . |
| 4,324,427 | 4/1982 | Buttaravoli . |
| 4,327,719 | 5/1982 | Childers . |
| 4,340,040 | 7/1982 | Straith . |
| 4,341,207 | 7/1982 | Steer et al. . |
| 4,341,208 | 7/1982 | Gordon . |
| 4,402,314 | 9/1983 | Goode . |
| 4,414,977 | 11/1983 | Rezakhany . |
| 4,440,231 | 4/1984 | Martin . |
| 4,485,809 | 12/1984 | Dellas . |
| 4,534,342 | 8/1985 | Paxa . |
| 4,592,357 | 6/1986 | Ersek . |
| 4,669,458 | 6/1987 | Abraham et al. . |
| 4,674,133 | 6/1987 | Oschner . |
| 4,744,355 | 5/1988 | Faasse, Jr. . |
| 4,823,789 | 4/1989 | Beisang, III . |
| 4,917,112 | 4/1990 | Kalt . |
| 4,932,943 | 6/1990 | Nowak . |
| 4,971,282 | 11/1990 | Dickinson . |
| 4,984,302 | 1/1991 | Lincoln . |
| 4,995,114 | 2/1991 | Price, Jr. . |
| 5,003,971 | 4/1991 | Buckley . |
| 5,022,389 | 6/1991 | Brennan . |
| 5,067,482 | 11/1991 | Reid . |
| 5,101,837 | 4/1992 | Perrin . |
| 5,116,675 | 5/1992 | Nash-Morgan . |
| 5,209,801 | 5/1993 | Smith . |
| 5,284,469 | 2/1994 | Jasen et al. . |
| 5,383,891 | 1/1995 | Walker . |
| 5,466,456 | 11/1995 | Glover . |
| 5,476,091 | 12/1995 | Johnson . |
| 5,479,944 | 1/1996 | Petruson . |
| 5,533,499 | 7/1996 | Johnson . |
| 5,533,503 | 7/1996 | Doubek et al. . |
| 5,546,929 | 8/1996 | Muchin . |
| 5,549,103 | 8/1996 | Johnson . |
| 5,553,605 | 9/1996 | Muchin . |
| 5,706,800 | 1/1998 | Cronk et al. ........................ 128/200.24 |
| 5,718,224 | 2/1998 | Muchin . |
| 5,735,272 | 4/1998 | Dillon et al. ...................... 128/DIG. 26 |
| 5,752,511 | 5/1998 | Simmons et al. ................. 128/DIG. 26 |
| 5,769,089 | 6/1998 | Hand et al. ........................ 128/200.24 |

FOREIGN PATENT DOCUMENTS

| | | |
|---|---|---|
| 1.001.434 | 2/1952 | France . |
| 1.046.299 | 12/1953 | France . |
| 1.182.602 | 6/1959 | France . |
| 1.351.537 | 12/1962 | France . |
| 381127 | 9/1923 | Germany . |
| 437661 | 11/1926 | Germany . |
| 453006 | 3/1928 | Germany . |
| 882601 | 7/1953 | Germany . |
| 3640979 A1 | 8/1987 | Germany . |
| 4 030 465 A1 | 4/1992 | Germany . |
| 289561 | 10/1985 | Spain . |
| 2504 | 11/1910 | United Kingdom . |
| 18254 | 11/1911 | United Kingdom . |
| 354998 | 8/1931 | United Kingdom . |
| 520491 | 4/1940 | United Kingdom . |
| 748326 | 4/1956 | United Kingdom . |
| 768488 | 2/1957 | United Kingdom . |
| 786488 | 11/1957 | United Kingdom . |
| 1 244 146 | 8/1971 | United Kingdom . |
| 1 435 853 | 5/1976 | United Kingdom . |
| 2 126 101A | 3/1984 | United Kingdom . |
| 2 217 206A | 10/1989 | United Kingdom . |
| WO88/03788 | 6/1988 | WIPO . |
| WO91/18567 | 12/1991 | WIPO . |
| WO92/22340 | 12/1992 | WIPO . |
| WO94/23675 | 10/1994 | WIPO . |

OTHER PUBLICATIONS

Petruson, Bjorn; "Snoring Can be Reduced When the Nasal Airflow is Increased by the Nasal Dilator Nozovent", *Archives of Ortolarngology—Head & Neck Surgery*, vol. 116, pp. 462–464 (Apr. 1990).

Petruson et al.; The Importance of Nose–Breathing for the Systolic Blood Pressure Rise During Exerise;, *Acta Otolaryngol*, Stockholm vol. 109, pp. 461–466 (1990).

E.N.T. Spring Symposium; "Report of a Symposium at the Royal Society of Medicine, London, May 21, 1991", pp., 1–4.Petruson et al.; "Two New Ways for Nasal Administratiuon of Drugs with the Nasal Dilator Nozovent", Abstract, ENT—Department, University of Goteberg, Sahlgren's Hospital, 413, 45 Goteborg, Sweden.

Ford, C.N. et al.; "A Nasal Prosthesis for Treatment of Nasal Airway Obstruction", *Rhinology*, vol. 23, pp. 223–229 (1985).

J.M. Lancer and A.S. Jones; "The Francis Alae Nasi Prop and Nasal Resistance to Airflow", *Journal of Laryngol, Otol.*, vol. 100, pp. 539–541 (1986).

Foreign language newspaper article, "Adne Har Nese . . . " (undated).

Foreign language newspaper article, "Enda Raskere Med Ring I Nesen?" (undated).

Foreign language newspaper article, "Skoytelopere Med Ring I Nesen . . . " (undated).

foreign language magazine artile, "Sagen in Der Nacht" (undated) (see entire document).

NON-LINEAR NASAL DILATOR

RELATED APPLICATIONS

This invention relates to application Ser. No. 08/499,636, filed Jul. 7, 1995; and Ser. No. 08/521,631, filed Aug. 31, 1995; Ser. No. 08/580,127, filed Dec. 28, 1995; and Ser. No. 08/698,002, filed Aug. 16, 1996. The contents of these applications are incorporated by reference herein.

BACKGROUND OF THE INVENTION

This invention relates to dilators for the nose. In particular, the invention is concerned with a dilator to urge the nasal passages of the nose open during breathing.

One known form of dilator used for this purpose is in the nature of a band for extension over the nose from one nasal passage, over the bridge of the nose, to the other nasal passage. This pad is formed of a flexible material which has sandwiched with it a resilient spring material. Both the flexible material and the spring are normally planar. When the pad is placed on the nose, it sticks to the skin of the nose, and the action of the spring causes the nasal passages to be urged open.

In the Applicant's experience, the known dilator is not as effective as it could be. In particular, the nasal passages are not urged open as much or as little as they could usefully and safely be opened. Also, the currently known device consists of multiple components forming the pad in a sandwich relationship with the spring. Therefore, the fabrication of such a dilator arrangement is unduly complicated.

There is a need to provide a pad system for a dilator for location over the nose which minimizes the disadvantages of known systems.

SUMMARY OF THE INVENTION

By this invention there is provided a dilator which has advantages over known dilators.

According to the invention a nasal dilator includes an elongated normally planar spring member for bridging a human nose. The spring member has an outer edge and opposite flat surfaces and is for extending over a bridge of the nose and for being urged from the planar position so as to engage the user's nose. The tension in the spring will act to cause the dilation of the nasal passages, as the spring tries to move back towards its planar state. The spring member has an outer edge having a high point for location substantially centrally over the bridge of the nose and low points to either side of the high point. Preferably, the low points depend downwardly from the high point. The high point and low point terminology is used to indicate a non-linear profile.

There is also a flexible pad having a surface area and peripheral edge. The pad, which is made of a breathable material, engages the spring member, which is a polyflex material, and extends around the spring member. Preferably, the spring and the pad are relatively arcuate or curved in shape, along their respective longitudinal sides. As such, the dilator has a non-linear profile.

There is an adhesive between the spring member and the pad such that the spring member on one of its entire engaging surfaces wholly adheres with the pad. A surface perimeter area of the pad is formed between the outer edge of the spring member and the peripheral edge of the pad. The surface perimeter area includes an adhesive for adhering to skin of the nose.

When the spring member is located over the bridge of the nose, the opposite flat surfaces of the spring member extend over the bridge of the nose and at least partly beyond the bridge of the nose. In this manner, the spring extends over the nasal passages on both sides of the bridge.

In some embodiments, when in use on the nose, there are only the spring member, the adhesive pad, and the adhesive between the pad and the spring member. When in position on the nose, a flat surface of the spring member without adhesive engages directly on the nose. In some other embodiments, there is also an adhesive on the surface area of the spring adjacent to the bridge of the nose, so the spring member adheres to the nose.

When there is a pad, the pad includes a protrusion from one side and substantially centrally located between the pad ends for facilitating centralized placement of the pad on the nose. The protrusion includes a rounded perimeter and is formed from one side of the pad, and the protrusion extends longitudinally between about one sixth and about one quarter of the length of the one side of the pad. The ends of the pad are rounded.

In different forms there may only be the spring for engagement on the nose. Further, there could be forms where the spring is located on the pad on the opposite side of the pad intended for engagement with the nose, and here the pad wholly adheres to the nose.

In different embodiments, there are situations where at least one of, and preferably all of the components, namely pad, adhesive and spring are substantially transparent, translucent, clear, a flesh-like color or shade so as to effectively blend with the skin of wearer. In other preferred situations the pad is effectively colored or rendered ornate or patterned, at least on its surface removed from the nose side.

The dilator can be at least partly formed of transparent or clear material so as to enhance its cosmetic appearance on the nose. Ornamentation can be provided to one surface of the spring thereby to be visible through a transparent pad. Alternatively or additionally, the pad can be imprinted with ornamentation.

In yet other preferred forms of the invention, the pad is substantially transparent, and the spring is colored or patterned on its surface removed from the nose. The pattern can be a product logo. Coloring can represent a team color. The spring can be at least partly visible through the pad.

When unattached to the nose, the spring member and pad, has a natural position which is planar. This planar position is contrary to a curvature formed by location of the spring member over the bridge of the nose and adjacent to the nasal passages. Alternatively, the natural position is with a curvature contrary to the shape of the curvature formed from one nasal passage over the bridge to the second nasal passage. The contrary curvature acts to place an increased amount of spring action on the dilator so that the dilation action on the nasal passages is enhanced when in use.

A dilator with a curved or arcuate shape allows a better ergonomic fit onto the nose compared to nasal dilators of linear design or construction. Further, a dilator with rounded ends provide a more comfortable fit to the nose compared to dilators whose ends have sharp or more defined corners. The protrusion advantageously enables the user to more easily position the dilator on the nose.

Because the spring of the dilator does not extend the full length of its attached pad, the dilator is able to accommodate or fit greater diversity of nose sizes (since the spring remains in contact with the alar or soft tissue of the nose) compared to other dilators of comparable length whose springs traverse the length of the pad.

The invention is further described with reference to the accompanying drawings.

DETAILED DESCRIPTION OF THE INVENTION

Figure 1:
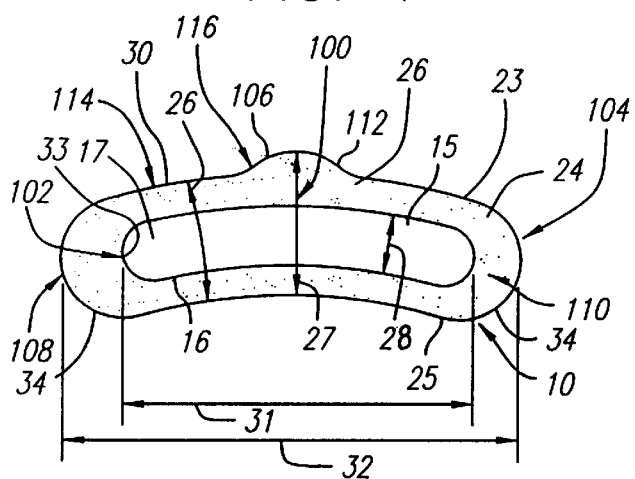
FIG. 1 is an underview of the dilator showing adhesive on the pad and on the spring, where the spring is for location between the nose and the pad.

A nasal dilator 10 prevents the outer wall tissue 11 of first and second nasal passages 12 and 13, respectively, of a human nose 14 from drawing in during breathing.

SPRING

The dilator 10 includes an elongated arcuately shaped resilient spring 15 for bridging the human nose 14. The spring member is shaped between a high point 100 for location substantially centrally over the bridge of the nose and low points 102 and 104 to either side of the high point 100 and for depending downwardly from the high point 100. The spring member 15 can be formed of a synthetic resinous material. The spring member 15 has an outer edge 16 and opposite flat surfaces 17 and 18. The surface 17 extends over a bridge 19 of the nose 14.

The spring material 15 is formed of about 0.010 inch clear polyester film or clear polyethylene terephthalate film or polystyrene film. An acrylic adhesive carrier 20 can be a double-sided adhesive coated polyethylene film having a thickness of about 0.0015" liner for die cutting is provided on one side of spring 15. The adhesive is indicated by numerals 21 and 22.

In other situations, the film is white or colored on at least one of surfaces 17 or 18. The surface 18 can have a logo pattern printed on the face. Alternatively, different patterns, shapes, words, and letters can be used.

The spring 15 is clear, durable, and has dimensional stability. It is resistant to mild acids, alkalis, and salt. Further, the spring 15 can be fungus, water and corrosion-resistant.

PAD

The dilator 10 includes a flexible adhesive pad 23 having a surface area 24 and peripheral edge 25. The pad 23 engages the spring member 15 and extending around the spring member 15. The pad defines a shape between a high point 106 for location substantially centrally over the bridge 19 of the nose and low points 108 and 110 to either side of the high point 100 and for depending downwardly from the high point. The pad includes a protrusion 112 from one side 114 of the pad and substantially centrally located between the ends 34 for facilitating centralized placement of the pad 23 on the nose. The protrusion 112 includes a rounded perimeter 116 and is formed from one side 114 of the pad 23, and the protrusion extends in length between about one sixth and about one quarter of the length of the one side of the pad. Also, the ends 34 of the pad 23 are rounded.

The pad material 23 is preferably from Avery Dennison Specilaties Tape Division, Chicago, Ill. 60693. The product is a tan elastic polyurethane tape coated on one side with an acrylate adhesive 26, or a non-woven polyethylene film material coated on one side with an adhesive such as an acrylic adhesive. The tape is supplied on a paper liner with the liner on the inside of the roll.

In other situations, the pad material is substantially transparent, translucent, clear or colored, for instance, to conform to a flesh color or tone.

When the pad 23 is transparent and the spring is colored, patterned or imprinted with a logo or the like, this imprintation is visible through the transparent pad 23. Thus, when worn on the nose 14, there is the appearance of a colored device, in part in whole, or of different combinations of pad and spring. The spring can thus be used as carrier of a message and not only for its resilient characteristics.

The backing of the tape is nonwoven of tan-colored polyurethane fibers. The adhesive 26 is a hypoallergenic, pressure-sensitive acrylate.

SPRING AND PAD

The spring member 15 occupies about 20% to about 60% of the surface area 24 of the pad 23. The spring member 15 is centrally located in the surface area 24 of the pad 23.

The peripheral edge 25 of the pad 23 effectively defines two portions of narrow width 26 and a central broad width 27. The broad width 27 which incorporates the protrusion 112 is substantially for location over the bridge 19 of the nose 14. The narrow widths 26 are substantially for location centrally over the nasal passages 12 and 13 of the nose 14.

The spring member 15 defines a width 28. The width 28 of the spring member 15 being about one-half to three-quarters of the width of narrow width 26 of the pad 23. The pad 23 is an elongated element with rounded ends 34.

The spring member 15 defines a length 31 and the pad 23 defines a length 32. The spring member 15 is centrally located along the length 32 of the pad 23. The length 31 of the spring member 15 is between about one-half to three-quarters of the length 32 of the pad 23.

The spring member 15 and the pad 23, respectively, include ends 33 and 34. The ends 33 of the spring member 15 are located inwardly from the ends 34 of the pad member 23.

ADHESIVE & LINER

The adhesive 26 is located between the spring member 15 and the backing of the pad 23 such that the entire engaging surface 18 of the spring member 15 wholly adheres with the pad 23.

In the embodiments using a transparent or clear pad 23, it is desirable to have the adhesive 26 substantially clear in color. This is particularly the case where there is an imprintation on the spring surface 18.

A surface perimeter area 30 of the pad 23 is formed between the outer edge 16 of the spring member 15 and the peripheral edge 25 of the pad 23. The surface perimeter area 30 includes the adhesive 26 for adhering to skin of the nose 14.

The surface area 17 of the spring 15 includes an adhesive carrier 20 for adhering to the skin of the nose 14.

The adhesive carrier system is preferably No. 1509, Double Coated Medical Tape on Liner from 3M Company, 3M Center, St. Paul, Minn. This product is a double-coated transparent polyethylene film, coated on both sides with a hypoallergenic, pressure-sensitive, acrylate adhesive, supplied on a paper liner. The double coated tape is wound with the liner on the outside of the roll.

The carrier is transparent 3 mil polyethylene film; the adhesive is hypoallergenic, pressure-sensitive acrylate; and the liner is bleached Kraft-Glassine paper, silicone coated on both sides.

USING THE DILATOR

Figure 3:
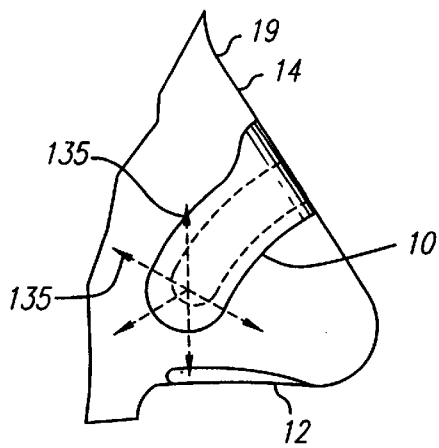
FIG. 3 is a side view of the dilator, being a spring and pad on the nose, and wherein the spring is located between the pad and the nose.
Figure 5:
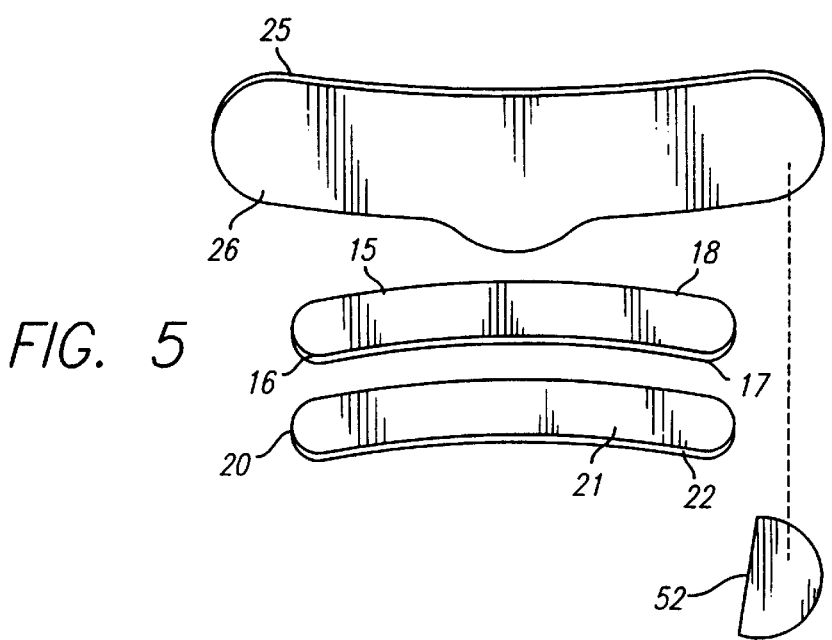
FIG. 5 is an exploded perspective top view of the components of FIG. 1 making up the dilator.
Figure 6:
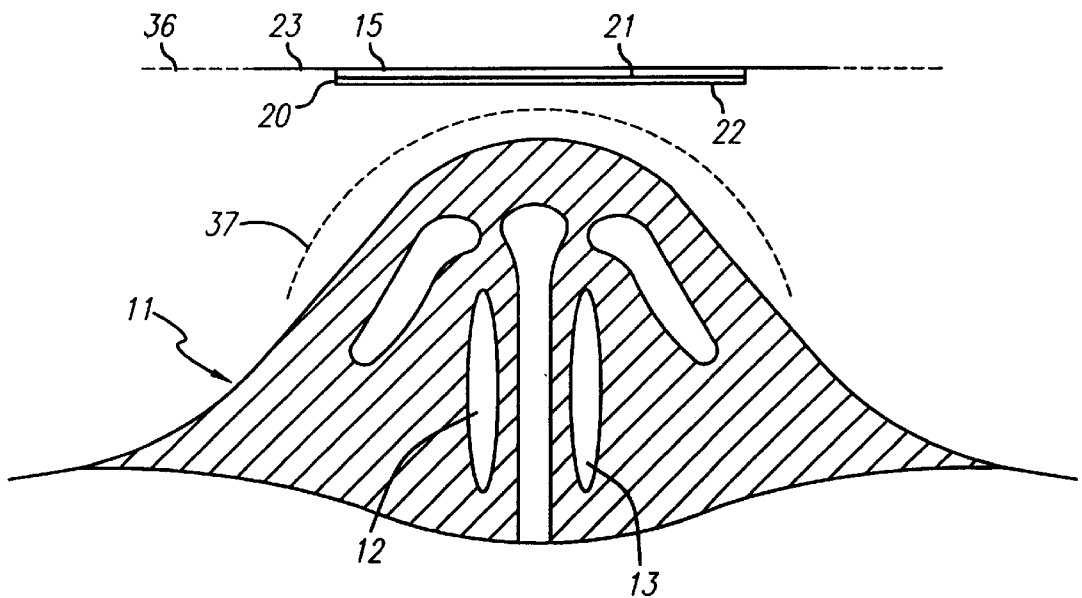
FIG. 6 is a cross-sectional view through the nose showing a dilator in a relatively removed position before usage and the nasal passages closed.

As illustrated in FIG. 3 when the spring member 15 is located over the bridge 19 of the nose 14, the opposite flat surfaces 17 and 18 (shown in FIG. 5) of the spring member 15 extend over the bridge 19 of the nose 14 and at least partly beyond the bridge 19 on both sides of the bridge 19.

In use on the nose 14, there are only the spring member 15, and the adhesive pad 23. There is the adhesive 26 between the pad 23 and the spring member 15, and selectively, in one form of the invention there is also the adhesive carrier 20 on the surface 17 of the spring member 15.

When the pad member 23 is located on the nose 14 of a wearer, the ends 33 of the spring 15 are urged outwardly as indicated by arrows 135 to separate from the skin covering the nasal passages 12 and 13 of the wearer. The pad 23 is lifted in part from the outer wall tissue 11 to open the nasal passages 12 and 13 in the vicinity of the ends 33 of the spring member 15. When in position on the nose 14, a flat surface 17 of the spring member 15 engages directly on the nose 14 through an adhesive 22.

Figure 7:
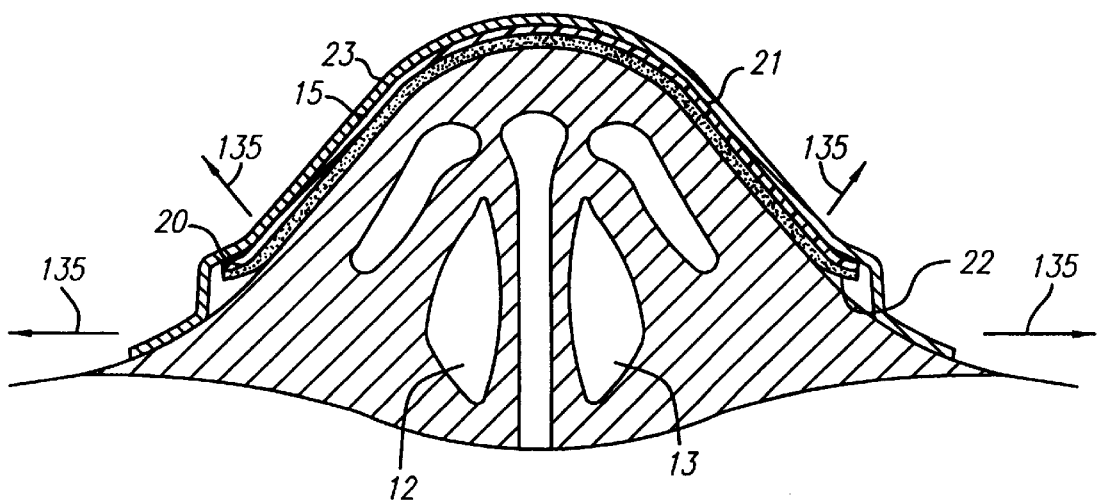
FIG. 7 is a cross-sectional view through the nose showing a dilator in position on the nose and the nasal passages opened.

Also as shown in FIG. 7, there is a force 135 which is applied to the skin of the outer wall tissue 11 of the nose 14 from positions along a line 136 where the pad adheres to the nasal skin. This line 136 is slightly removed from the perimeter of the spring 15, and the force 135 is directed at different angles from the nose. The pulling force 135 is spread broadly around the nasal skin and increases the overall opening force on the nasal passages 12 and 13.

Figure 2:
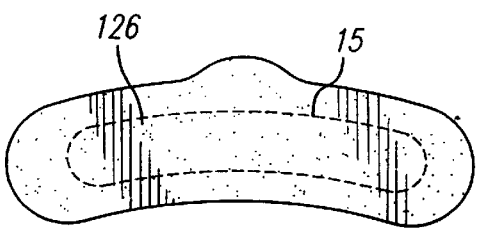
FIG. 2 is an underview of a different embodiment of the dilator where the spring is for location on the side of the pad opposite the side engaging the nose.

As illustrated in FIG. 2 there is embodiment where the spring member 15 is placed on the opposite side of the pad 23. In this embodiment the entire adhesive surface 126 of the pad engages the nose and the spring member 15 is remotely located on the opposite side of the pad.

Figure 4:
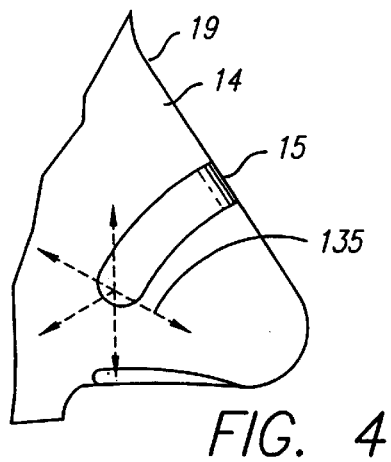
FIG. 4 is a side view of a third embodiment of the dilator on the nose, namely dilator which is a spring without the pad.

In FIG. 4 they have shown an embodiment where only the spring member 15 is used on the nose. In this embodiment, adhesive 21 is provided on one side of spring 15. There is no pad 23 use in that embodiment.

DILATOR PRIOR TO USAGE

When unattached to the nose 14, the spring member 15 and pad 23 have a natural position which is substantially planar, namely contrary to a curvature formed by location of the spring member 15 over the bridge 19 of the nose 14 and adjacent to the nasal passages 12 and 13. The resilient spring member 15 and pad 23 preferably have a planar position 36 contrary to the shape of the curvature 37 formed from one nasal passage 12 over the bridge 19 to the second nasal passage 13. The planar position 36 acts to place a requisite amount of spring action on the dilator 10 so that the dilation action on the nasal passages 12 and 13 is imparted when in use as the spring tries to return to its planar position.

MANUFACTURING THE DILATOR

The method of manufacturing for the dilator 10 requires the resilient spring member 15 to be die cut and located as an island within the surface area 30 of the pad 23.

The various materials: spring 15, pad 23, and adhesive 20, are provided, respectively, on rolls 41, 42 and 43 of material. The resilient spring 15 is formed of a ribbon material 44 which is die cut at 45 from ribbon material 44. The pad 23 is die cut at 46 from a second ribbon 47 of material. The release liner 152 removed from the pad 23 is removed as a ribbon to the waste liner roll 53.

The ribbon of resilient material 44 and pad material 47 are adhesively joined together in a webbing operation. The adhesive material 43 in the form of a ribbon 48 is fed into a position at die 45 on one side of the ribbon material 44 so as to place an adhesive on the ribbon material 44 for the spring. The adhesive system 20 is cut at die 45 to conform with the spring 15.

Adhesive 26 on the one side of the pad ribbon material 47 sticks the spring ribbon material 44 to the pad ribbon material 47 at the die 46.

Figure 8:
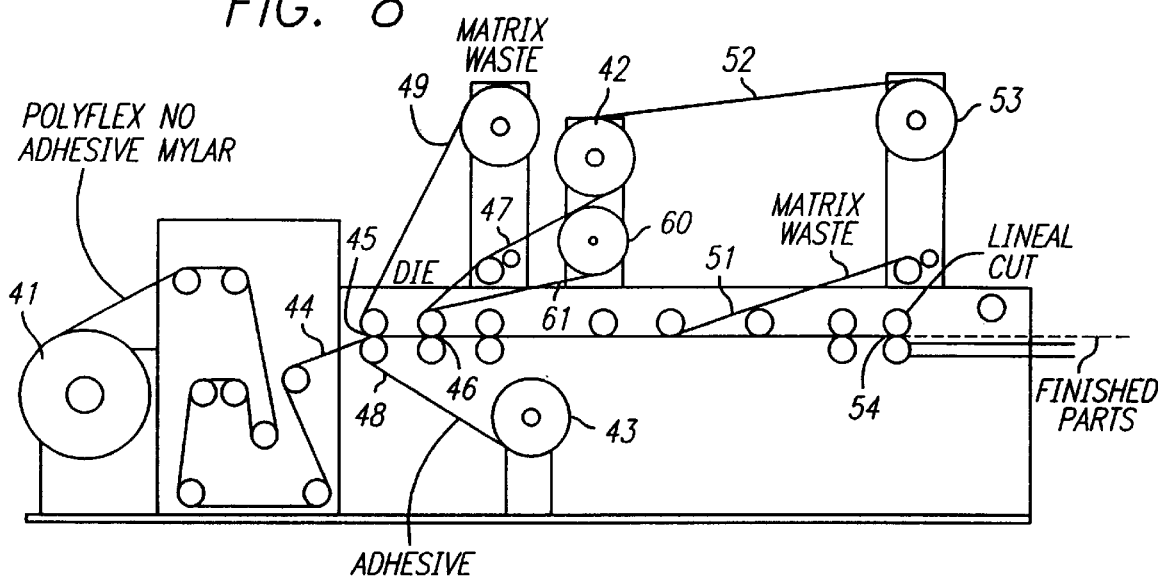
FIG. 8 is a diagrammatic view of a construction procedure for manufacturing the dilator.
Figure 8A:
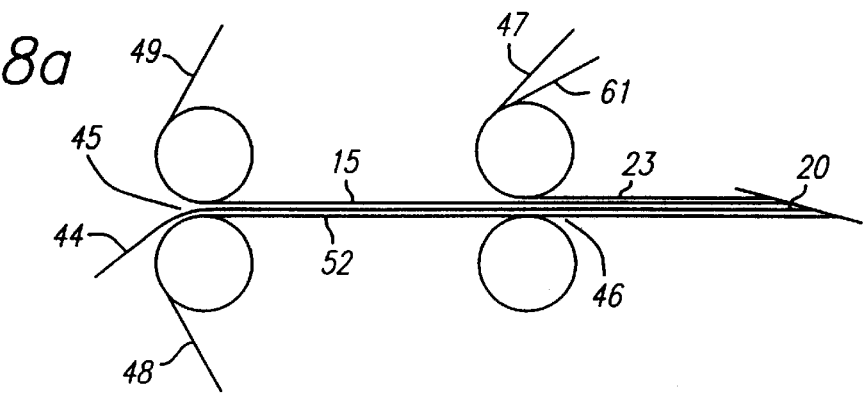
FIG. 8A illustrates side views of the dilator respectively at two different die positions in the construction procedure.

Non-adhering materials, 49, and 51 removed from the respective die cuts 45 and 46 are removed as ribbons of waste material. The material 49 is the unused ribbon material 44, namely the unused resilient material, and unused adhesive 48 which is die-cut 45. The material 51 is the spring 15, the pad 23, and the adhesive 20 which is die-cut 46. FIG. 8A illustrates the sandwiched components of the dilator at the die positions 45 and 46 respectively.

A liner 52 is also provided to cover the adhesive 26 of the pad 23 not covered by the spring 15. The liner is the leftover after the die-cut 45 of the resilient adhesive combination. When in use, the liner 52 is removed to expose the adhesive surface 26 and spring 15. The liner 52 is formed as the paper backing for the two sided adhesive 21 and 22 on carrier 20. The liner 52 is formed as the base of the roll of material 43 for the adhesive ribbon 48.

In some cases, the adhesive ribbon material 48 affixed to the spring ribbon material 44 may be avoided. There may be only the adhesive pad material 47 and the spring ribbon material 44 and a liner provided by a different ribbon material from roll 43. Thus only a paper type liner may be provided from roll 43. In such a situation there is no two sided coated tape.

Multiple dilators 10 are formed in a nested series in the manufacturing process through dies 45 and 46. They are then cut and separated at die 54 prior to packaging.

Figure 9:
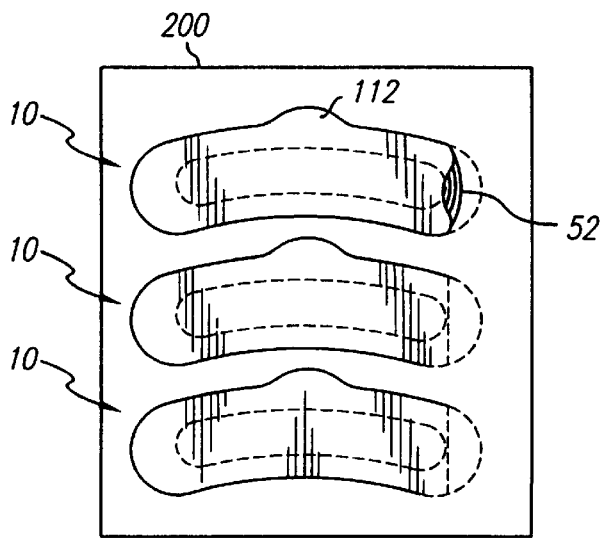
FIG. 9 is a view of multiple dilators mounted on a release liner.

As shown in FIG. 9, three dilators 10 are adhesively mounted onto a release liner. There is a first release liner 200 for securing the dilator prior to use, and a second release liner 52 engaging a tip portion of the pad 23, namely less than the whole pad. The second release liner 52 overlaps the first release liner 200 thereby to facilitate release of the pad 23 from the first release liner 200. This is the format on which the dilators leave the manufacturing process. The dilators are stacked in adjacent relationship on the first release liner 200. At the one end of each flexible pad, there is a second release liner 52 which is located at the tip of the pad 23. This second release liner 52 is sandwiched between the flexible pad 23 and the first release liner 200, and facilitates removing the entire dilator together with the second release liner 52 from the first release liner 200 when each dilator is to be used. The second release liner 52 is then removed from the adhesive end 26 of the flexible pad 23 when the user places the dilator the nose. The liners 200 and 52 are a silicone-coated kraft paper. This tab would be added to the pad raw material just before the raw material is laminated to the nylon spring. Roller 60 has the tab material which is directed along line 61 to roller 46 for lamination. Other ways can be used for adding the tab, for instance, it can be added off-line to the pad before the sandwiching of the different components.

EXAMPLE DILATORS

Two examples of a dilator configuration are described. In the first example, the characteristics are as follows:

EXAMPLE 1

This would be a dilator suitable for the size of an average male's nose.

The straight length (32) of the pad from end to end is about 2.25 inches.

The straight length (31) of the spring from end to end is about 1.69 inches.

The radius of the arcuate sides of the pad is about 2.85 inches.

The radius at the rounded ends of the pad is about 0.3 inches.

The width (28) of the spring member is about 0.25 inches.

The height of the protrusion from the one side of the pad is about 0.14 inches.

The radius of the protrusion is about 0.36 inches.

EXAMPLE 2

This would be a dilator suitable for the size of an average female's nose.

The straight length (32) of the pad from end to end is about 1.87 inches.

The straight length (31) of the spring from end to end is about 1.40 inches.

The radius of the arcuate sides of the pad is about 2.37 inches.

The radius at the rounded ends of the pad are about 0.25 inches.

The width (28) of the spring member is about 0.23 inches.

The height of the protrusion from the one side of the pad is about 0.12 inches.

The radius of the protrusion is about 0.30 inches.

GENERAL

Many other forms of the invention exist, each differing from others in matters of detail.

In some cases, the dilator prior to use is planar. For instance, in some uses of the dilator on the nose, there are may be elements in addition to the basic spring member, the adhesive pad, and the adhesive between the spring and the nose skin. Also, there are situations where the adhesive on the spring for engaging the nose is unnecessary.

In one aspect of the nasal dilator 10, all the components located on the nose 14 are substantially transparent translucent or clear. Thus, the spring 15 is transparent as are the adhesive carrier 20 and adhesive layers 21 and 22. So too is the pad 23 and adhesive 26 transparent. Thus, when the dilator 10 is located on the nose, it substantially blends with the nose color and/or is substantially invisible. As such, the dilator 10 is a cosmetic improvement over prior dilators.

In other situations, the pad may be partly transparent, or translucent, so that the spring can be seen through the pad. In yet other situations, the pad and/or spring can be made of different target colors to provide colorful combinations of pad and spring. Further, although the pad is indicated to be plastic, there could be situations where it is formed of cotton or some other material.

In other situations the pad is ornamented. The pad is selectively not transparent, and the spring can not be seen when worn. In other situations, the one surface of the spring is ornamented and this ornamentation can be seen through the transparent pad. The dilator can be printed and/or tinted by any known process. This can be, for instance, silk screening, flexography, or gravure.

Although the invention in its mode with at least partly transparent components has been described with reference to two components, a pad and a spring with adhesive as required, there could be situations where there are multiple springs and/or pads. In some case, the springs may be located on the pad on the side removed from the nose. A further covering element may cover the spring. Further there are situations where there are only a spring and there are situations where the spring is located on the remote side of the pad, namely opposite to the side of the nose.

The resilient member and other components of the dilator can be packaged in a bent, curved or straight condition, and can be in that static planar condition before dilator application to the nose.

In some other situations, instead of applying the adhesives on a 3 inch film, it can be coated onto the pad.

Also, there can be situations where only one side of the pad and/or one side of the spring are curved or has a non-linear profile. There can be situations where the pad profile is curved and the spring profile is straight, or alternatively the pad profile is straight and the spring profile is curved. Although the examples show curved sides, there can be situations where the sides are straight, but are downwardly directed from the high point or apex intended to be centrally over the nose. Instead of a protrusion, there could be a cut out in the pad for indicating centralization, and instead of being at the top side it could be at the underside.

There could also be situations where the dilation is intended to be used with the high point towards the end of tip of the nose and the sides depend in a sense upwardly towards the alar or soft tissue of the nose. In such a configuration, the profile of the dilator is in a sense reversed. Thus, the apex or high point is at the "bottom" or lower portion of the nose and the low points are at a location "above" the apex.

In yet other forms of the invention, there may be only a single layer dilator having a spring with the defined profile and adhesive to secure the spring to the nose.

In yet other situations, there could be multiple high points and low points in the non-linear profile.

The invention is to be determined solely in terms of the following claims.

What is claimed is:

1. A nasal dilator for preventing outer wall tissue of nasal passages of a human nose from drawing in during breathing, consisting of:

an elongated curved spring member for bridging a human nose, the spring member having an outer top curved edge, an outer curved bottom edge, two opposite ends connecting the respective top and bottom edges, the two edges being substantially parallel to each other from one end to the opposite end, and opposite flat surfaces and being for extending over a bridge of the nose and being for engaging the user's nose, wherein the spring member has the outer top edge having a high point for location substantially centrally over the bridge of the nose and low points to either side of the high point;

a flexible pad having a surface area and peripheral edge, the pad being for engaging the spring member and extending around the spring member so that there is a surface perimeter area of the pad formed between the outer edge of the spring member and the peripheral edge of the pad, the spring being inset from the peripheral edge of the pad substantially around the pad, and wherein the surface perimeter area includes an adhesive for adhering to skin of the nose; and an adhesive means between the spring member and the pad such that the spring member on one of its flat surfaces adheres with the pad, the arrangement being such that when the spring member is located over the bridge of the nose, the opposite flat surface of the spring member extends over the bridge of the nose and at least partly beyond the bridge on both sides of the bridge, and the surface perimeter area of the pad adheres to the skin of the nose.

2. A dilator as claimed in claim 1, wherein the adhesive means for permitting the pad to adhere to the skin of the nose is effected by having the spring member occupy between about 25% to about 50% of the surface area of the pad.

3. A dilator as claimed in claim 1 wherein the adhesive means for permitting the pad to adhere to the skin of the nose is effected by having the spring member be centrally located in the surface area of the pad, and the surface of the spring member be between about one-quarter to about half of the surface area of the pad.

4. A dilator as claimed in claim 1 wherein the adhesive means for permitting the pad to adhere to the skin of the nose is effected by having the spring member define a length and the pad define a length, the spring member being centrally located along the length of the pad, and the length of the spring member be between about one-half to about three-quarters of the length of the pad.

5. A dilator as claimed in claim 1 wherein the pad defines a shape between a high point for location substantially centrally over the bridge of the nose and low points to either side of the high point and for depending downwardly from the high point.

6. A dilator as claimed in anyone of claims 1 to 5 wherein, in use on the nose, there are the spring member, the adhesive pad, the adhesive between the pad and the spring member, and means for adhering such spring member directly to the user's nose including an adhesive on the spring member, and the pad and the spring have rounded ends.

7. A dilator as claimed in claim 1 wherein, when in position on the nose, a flat surface of the spring member engages directly on the nose.

8. A nasal dilator for preventing outer wall tissue of nasal passages of a human nose from drawing in during breathing consisting of:

an elongated curved substantially planar spring member for bridging a human nose, the spring member having an outer curved top edge, an outer curved bottom edge, two opposite ends connecting the respective top and bottom edges, the two edges being substantially parallel to each other from end to end, and opposite flat surfaces and being for extending over a bridge of the nose and being for engaging the user's nose, wherein the spring member has an outer edge having a high point for location substantially centrally over the bridge of the nose and low points to either side of the high point; and an adhesive for adhering the spring to skin of the nose, and the spring being for being urged under tension from its planar position to thereby engage the skin of the nose, such that tension in the spring when it engages the nose tends to return the spring to a planar relationship and thereby cause dilation of the nasal passages with which the spring adheres.

9. A nasal dilator for preventing outer wall tissue of nasal passages of a human nose from drawing in during breathing, comprising:

an elongated substantially arcuate spring member for bridging a human nose, the spring member having an outer arcuate top edge, an outer arcuate bottom edge, two opposite ends connecting the respective top and bottom edges, the two edges being substantially parallel to each other from end to end, and opposite flat surfaces and being for extending over a bridge of the nose;

a substantially arcuate flexible pad having a surface area and peripheral edge, the pad being for engaging the spring member and extending around the spring member so that there is a surface perimeter area of the pad formed between the outer edge of the spring member and the peripheral edge of the pad whereby the spring is inset from the peripheral edge of the pad substantially around the pad, and wherein the surface perimeter area includes an adhesive for adhering to skin of the nose and for adhering the spring member to the pad; and the pad includes a protrusion to extend from one side and substantially centrally located between the ends for facilitating centralized placement of the pad on the nose.

10. A dilator as claimed as claimed in claim 9, wherein the protrusion includes a rounded perimeter and is formed to extend from one side of the pad, and the pad and the spring have rounded ends.

11. A dilator as claimed in claim 10, wherein the protrusion extends between about one sixth and one quarter of the length of the one side of the pad.

* * * * *